(12) United States Patent
Vartak et al.

(10) Patent No.: US 9,568,416 B2
(45) Date of Patent: Feb. 14, 2017

(54) MULTIMODE SYSTEMS AND METHODS FOR DETECTING A SAMPLE

(75) Inventors: Sameer Dinkar Vartak, Bangalore (IN); Sandip Maity, Bangalore (IN); Rajesh Veera Venkata Lakshmi Langoju, Bangalore (IN); Abhijit Vishwas Patil, Bangalore (IN)

(73) Assignee: General Electric Company, Niskayuna, NY (US)

( * ) Notice: Subject to any disclaimer, the term of this patent is extended or adjusted under 35 U.S.C. 154(b) by 763 days.

(21) Appl. No.: 13/334,825

(22) Filed: Dec. 22, 2011

(65) Prior Publication Data
US 2013/0165329 A1    Jun. 27, 2013

(51) Int. Cl.
*G01N 21/25* (2006.01)
*G01N 21/552* (2014.01)

(52) U.S. Cl.
CPC .......... *G01N 21/253* (2013.01); *G01N 21/553* (2013.01); *G01N 21/554* (2013.01)

(58) Field of Classification Search
CPC .................................................... C40B 30/04
USPC ...................................................... 435/283.1
See application file for complete search history.

(56) References Cited

U.S. PATENT DOCUMENTS

| 6,579,721 | B1 | 6/2003 | Natan et al. | |
|---|---|---|---|---|
| 7,361,472 | B2 | 4/2008 | Yguerabide et al. | |
| 2002/0021485 | A1* | 2/2002 | Pilossof | 359/295 |
| 2002/0140801 | A1* | 10/2002 | kubota | B41J 2/465 347/239 |
| 2005/0179895 | A1* | 8/2005 | Puppels | G01J 3/447 356/328 |
| 2007/0057159 | A1 | 3/2007 | Hing | |
| 2009/0262355 | A1 | 10/2009 | Boeschoten et al. | |
| 2011/0273721 | A1* | 11/2011 | Kulkarni et al. | 356/479 |
| 2012/0105852 | A1* | 5/2012 | Patil et al. | 356/445 |

OTHER PUBLICATIONS

Nenninger et al., "Long-Range Surface Plasmons for High-Resolution Surface Plasmon Resonance Sensors", Sensors and Actuators B: Chemical, vol. 74, Issues 1-3, pp. 145-151, Apr. 15, 2001.
Cunningham et al., "Colorimetric Resonant Reflection as a Direct Biochemical Assay Technique", Sensors and Actuators B: Chemical, vol. 81, Issues 2-3, Jan. 5, 2002.
So et al., "Surface Plasmon Resonance Imaging-Based Protein Arrays for High-Throughput Screening of Protein-Protein Interaction Inhibitors", Proteomics, vol. 5, Issue 17, pp. 4427-4431, 2005.
Boecker et al., Differential Surface Plasmon Resonance Imaging for High-Throughput Bioanalyses, Analytical Chemistry, vol. 79, pp. 702-709, 2007.
Homola, "Surface Plasmon Resonance Sensors for Detection of Chemical and Biological Species", Chemical Reviews, vol. 108, pp. 462-493, 2008.
Christopher et al., "SPR Imaging for High Throughput, Label-Free Interaction Analysis", Combinatorial Chemistry & High throughput screening, vol. 12, pp. 741-751, Sep. 2009.

* cited by examiner

*Primary Examiner* — Christopher M Gross
(74) *Attorney, Agent, or Firm* — Seema S. Katragadda

(57) ABSTRACT

A multimode detection system for detecting one or more samples is provided. The detection system comprises an electromagnetic radiation source, a reference arm, and a sample arm comprising a sensing substrate having a plurality of sample fields, wherein the sample fields are configured to receive the one or more samples. The system further comprises a phase difference generator configured to introduce pathlength differences in the reference arm, sample arm, or both, a spatial light modulator operatively coupled to the reference arm, sample arm, or both, wherein the spatial light modulator is configured to modulate incident radiation, resultant radiation, or both in the reference arm, sample arm, or both, and an imaging spectrometer configured to discriminate between two or more spatially separated sample en two or more spatially separated sample fields.

16 Claims, 6 Drawing Sheets

MULTIMODE SYSTEMS AND METHODS FOR DETECTING A SAMPLE

BACKGROUND

The invention relates to detection and imaging, and more particularly to systems and methods for detection and imaging of one or more samples.

In bio-sensing applications, such as drug discovery and proteomics research, a detection process starts with screening a vast number (a few thousands) of candidates in the form of ligand-receptor or protein-protein interactions that need to be rapidly examined. The screening of the candidates is generally carried out by detection systems that are suitable for high throughput operations, or by configuring a detection system such that it is suitable for high throughput operations. Subsequent to the screening step which is performed at a moderate resolution, a different detection system or detection configuration may be used for a low throughput and high resolution detection. The low throughput and high resolution detection may be used to perform detailed and relatively more reliable detection. Among other changes, reconfiguration of the detection systems may comprise changing one or more components of the system, such as a sensor chip on which the samples are disposed, a fluidic chip that supplies samples to the sensor chip, an optical arrangement of the system, or a detector. Reconfiguration of the system from the low to high resolution may provide enhanced analysis results, however, the reconfiguration of the system results in expensive and time consuming analysis. For example, in some instances switching the resolution may require switching between two or more detection systems. Switching between the two or more detection systems may be time consuming and expensive. In other instances, switching the resolution may require reconfiguration within the detection system. The reconfiguration of the system may be labor intensive, time consuming and expensive.

Therefore, it is desirable to have time efficient and cost effective systems and methods for analysis of one or more samples, where the systems may be configured to operate at high throughput and low throughput modes, and where the systems may be configured to efficiently switch between the high and low resolution modes.

BRIEF DESCRIPTION

In one embodiment, a multimode detection system for detecting one or more samples is provided. The detection system comprises an electromagnetic radiation source, a reference arm, and a sample arm comprising a sensing substrate having a plurality of sample fields, wherein the sample fields are configured to receive the one or more samples. The system further comprises a phase difference generator configured to introduce pathlength differences in the reference arm, sample arm, or both, a spatial light modulator operatively coupled to the reference arm, sample arm, or both, wherein the spatial light modulator is configured to modulate incident radiation, resultant radiation, or both, in the reference arm, sample arm, or both, and an imaging spectrometer configured to discriminate between two or more spatially separated sample fields.

In another embodiment, a multimode detection system for detecting one or more samples is provided. The detection system comprises an electromagnetic radiation source, a reference arm, and a sample arm comprising a sensing substrate having a plurality of sample fields, wherein the sample fields are configured to receive the one or more samples. The system further comprises a fluidic device operatively coupled to the sensing substrate, where the fluidic device is configured to selectively dispose samples in one or more sample fields, a phase difference generator configured to introduce pathlength differences in the reference arm, sample arm, or both, a spatial light modulator operatively coupled to the reference arm, sample arm, or both, wherein the spatial light modulator is configured to modulate incident radiation, resultant radiation, or both in the reference arm, sample arm, or both, a dispersing element configured to receive the modulated light from the spatial light modulator, and a detector operatively coupled to the dispersing element for detecting the modulated light, wherein the dispersing element is configured to direct the modulated light to the detector.

In one example, a multimode method for detecting samples in an array of samples. The method comprises providing an incident reference radiation to provide resultant reference radiation, providing an incident sample radiation to provide resultant sample radiation, introducing a path length difference in the incident reference radiation, incident sample radiation, resultant reference radiation, resultant sample radiation, or a combination thereof, modulating the incident reference radiation, incident sample radiation, resultant reference radiation, resultant sample radiation, or a combination thereof, acquiring interference spectra formed by the modulated radiation, and reconstructing spectral characteristics of the one or more samples.

DRAWINGS

These and other features, aspects, and advantages of the invention will become better understood when the following detailed description is read with reference to the accompanying drawings in which like characters represent like parts throughout the drawings, wherein.

DETAILED DESCRIPTION

Figure 1:
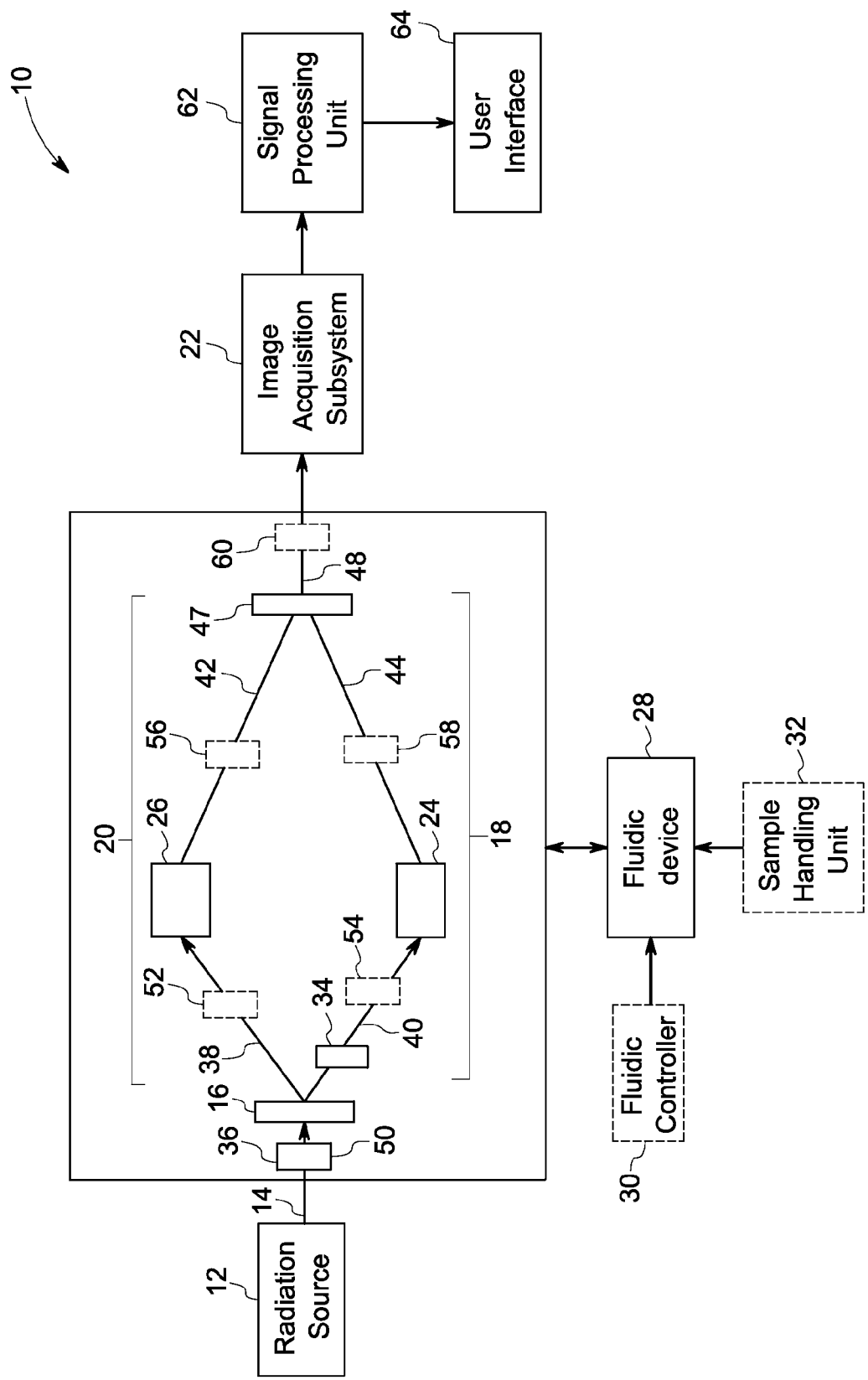
FIG. 1 is a block diagram of an example multimode detection and imaging system for detection of one or more samples.

Systems and methods for multimode detection and imaging of samples are provided. The systems and methods may be configured to efficiently switch between high and low throughput modes with minimal or no physical reconfiguration within the system. The systems and methods may be configured to select desirable resolution values for the modes of detection. In one example, the system may be configured to operate at a high throughput and moderate resolution mode. In another example, the system may be configured to operate at a low throughput and high resolution mode. In certain embodiments, the detection systems may be configured to simultaneously and selectively detect one or more samples in the array of samples. In one example, the systems may be configured to simultaneously detect an array of samples in a single shot or frame. In one embodiment, an image of spectral characteristics of the detected samples may be reconstructed.

In certain embodiments, a multimode detection system for detecting one or more samples is provided. The detection system comprises an electromagnetic radiation source, a reference arm, and a sample arm comprising a sensing substrate having a plurality of sample fields, where the sample fields are configured to receive the one or more samples. The system further comprises a phase difference generator configured to introduce pathlength differences in the reference arm, sample arm, or both, a spatial light modulator operatively coupled to the reference arm, sample arm, or both, where the spatial light modulator is configured to modulate incident radiation, resultant radiation, or both in the reference arm, sample arm, or both, and an imaging spectrometer configured to discriminate between two or more spatially separated sample fields.

The terms "a" and "an" do not denote a limitation of quantity, but rather denote the presence of at least one of the referenced item.

In one embodiment, the multimode detection system may be configured to operate at a desirable mode for a detection application at a given time. In one example, the system may switch between high and low throughput modes in a successive manner for a drug discovery application. The different throughput modes may be associated with corresponding resolution values. In one example, the detection system may operate at high throughput and low resolution mode, or a low throughput and high resolution mode depending on the type of analysis.

In one embodiment, the image of spectral characteristics of the detected samples may be reconstructed by introducing a spectral separation in the samples in a first direction (e.g., x-direction) also referred to as a "spatial direction", and imaging the array of samples in a second direction (e.g., y-direction), also referred to as an "imaging direction", where the second direction is different from the first direction. In the case of sample fields disposed in the form of an array, traversing along the spatial direction may provide a row, and traversing along the imaging direction may provide a column.

In certain embodiments, one or more samples may be provided for simultaneous detection of concentration of two or more different analytes in a solution, or concentration of a single analyte from two or more different analyte solutions. The multi-analyte format may also be used to detect the rate of reaction of the analytes in the solution.

FIG. 1 illustrates a multimode detection and imaging system 10 configured to selectively switch between two or more modes. The various modes of the system 10 may be associated with different throughput and resolution values. In one embodiment, a relative resolution for the high throughput mode may be lower than a relative resolution for the low throughput mode. In certain embodiments, the multimode detection system 10 may be an interferometric detection system. The interferometric detection system may comprise a Michelson or Mach Zhender configuration.

The system 10 comprises an electromagnetic radiation source 12 for providing electromagnetic radiation 14. The electromagnetic radiation source 12 may produce visible light, or near infrared light depending on the types of samples to be detected. Non-limiting examples of the radiation source 12 may comprise a light emitting diode, super luminescent light emitting diode, broadband light source, or a combination thereof. The broadband light source may emit continuous spectra over a range of wavelengths at any given point in time. The broadband light source may comprise sources such as, but not limited to, a tungsten lamp, white light source, xenon lamp, metal halide lamp, phosphor source, or a combination thereof.

The radiation 14 from the radiation source 12 may be directed to an optical engine 15. The optical engine 15 comprises a beam splitter 16, reference arm 18 and sample arm 20. The reference arm 18 may be defined by components and optical paths disposed between the radiation source 12 and an image acquisition subsystem 22 via a reference 24. For example, the reference arm 18 may comprise the reference 24, an optical path between the beam splitter 16 and the reference 24, and an optical path between the reference 24 and the image acquisition subsystem 22.

The sample arm 20 may be defined by components and optical paths disposed between the radiation source 12 and the image acquisition subsystem 22 via a sensing substrate 26. The sample arm 20 may comprise the sensing substrate 26, an optical path between the beam splitter 16 and the sensing substrate 26, and an optical path between the sensing substrate 26 and the image acquisition subsystem 22.

The sensing substrate 26 may comprise a plurality of sample fields for disposing the samples. The sample fields may be configured to selectively receive the samples. That is, the sample fields may be configured to receive the samples when the sample fields are disposed within a region of interest. The region of interest may be a region on the sensing substrate that comprises samples that are to be detected.

The sample fields may be disposed on the sensing substrate 26 as a one dimensional (1D) or two dimensional (2D) array. The samples may be disposed in some or all of the sample fields. For example, in the case of a high throughput mode, the samples may be disposed in all of the sample fields. In the case of a low throughput mode, the samples may be disposed in some of the sample fields. In one embodiment, one or more sample fields, configured to receive detectable samples, may be functionalized. In these embodiments, the sample fields may be immobilized with functionalizing material, such as ligand molecules.

A fluidic device 28, such as a microfluidic device or microfluidic chip, may be operatively coupled to the sensing substrate to provide samples to the sensing substrate. The fluidic device 28 may be configured to provide the samples to the corresponding sample fields on the sensing substrate.

A fluidic controller 30 may be provided to control the microfluidic operations of the fluidic device 28.

Optionally, a sample handling unit 32 may be operatively coupled to the fluidic device 28. The sample handling unit 32 may be coupled to fluid ports of the fluidic device 28 for transporting samples to and from the fluidic device 28, or carrying off waste flows from the fluidic device 28. The sample handling unit 32 may comprise chambers or reagent reservoirs for storing sample solution, flow through port for transporting samples, a pumping device, and a sample flow controller. The sample handling unit 32 may be configured to modify the transport of samples based on the detection of samples by the system 10. The sample handling unit 32 may be configured to accommodate a variety of samples including liquid, solid and gaseous samples. The sample handling unit 32 may comprise provisions for sample preparation and processing, such as, but not limited to, metering, mixing and diluting. The sample handling unit 32 may comprise a thermal element for heating or cooling the samples.

A phase difference may be introduced between the reference arm 18 and the sample arm 20 to spectrally detect the samples in the direction of the phase difference introduced. The phase difference may be introduced using a phase difference generator 34 as described in detail in U.S. patent application Ser. No. 12/914,622 titled "Systems and methods for detection and imaging of two-dimensional sample arrays", incorporated herein by reference. The phase difference generator 34 may comprise a dielectric material; a stack of glass plates, a liquid crystal, computer generated hologram, or a combination thereof.

In certain embodiments, the phase difference generator 34 may be disposed in the optical engine 15 for inducing a phase difference in the sample beam, reference beam, or both. The phase difference or a path length difference may be introduced in the incident radiation, or resultant radiation in the reference arm 18 or sample arm 20. In one example, the phase difference may be introduced in the incident reference radiation by disposing the phase difference generator 34 between the radiation source and the reference 24. The phase difference may be introduced in a direction other than an imaging direction. The phase difference may be used for spectral separation of the samples in the direction in which the phase difference is introduced. In embodiments where the phase difference is introduced in the incident radiation 14 or the resultant reflected radiation in a first direction, the sample fields in the first direction may be phase separated.

In the case of a 1D array of samples disposed along the spatial direction (row), the phase difference may be introduced in each of the samples in the 1D array of samples. In the case of a 2D array of samples comprising a plurality of rows (spatial direction) and columns (imaging direction), if the phase difference is introduced in each sample of a row, the samples of a particular column may comprise similar phase. In this case, the imaging may be performed in the direction along the columns to separate the spectral characteristics of the sample fields disposed along the columns (imaging direction), while the phase difference introduced along the rows facilitates spatially separating the samples disposed along the rows.

A spatial light modulator 36 may be disposed in the optical path of the incident radiation or resultant radiation, or both. The spatial light modulator 36 may be configured to modulate the amount of radiation 14 travelling from the source 12 towards the beam splitter 16. In one embodiment, the spatial light modulator 36 may be configured to select a portion of the radiation 14 that is representative of a region of interest on the sensing substrate 26.

The radiation source 12 provides the radiation 14. The radiation 14 is directed towards the spatial light modulator 36. The modulated radiation is split in two parts at the beam splitter 16. A first portion 38 that may travel in the sample arm 20 and a second portion 40 that may travel in the reference arm 18. The portions 38 and 40 selectively irradiate samples and reference, respectively. Resultant sample radiation 42 and resultant reference radiation 44 may combine at a beam splitter 47 and form co-propagating radiation 48.

In certain embodiments, the spatial light modulator 36 may comprise a variable area light valve. The area of the light valve that allows the light from the sensing substrate to reach the image acquisition subsystem 22 may be adjusted to modulate the amount of radiation (co-propagating beams 48) reaching the image acquisition subsystem 22.

In one embodiment, the spatial light modulator 36 comprises a mechanical light valve, micro-mechanical light valve, non-mechanical light valve, or a combination thereof. The mechanical light valves may comprise moving components, whereas, the non-mechanical valves may comprise non-moving components.

Non-limiting examples of the mechanical light valve comprises micro-electro mechanical system (MEMS) based valve, micro-opto-electro-mechanical structures (MOEMS), a variable slit device, or a combination thereof. Non-limiting examples of the non-mechanical light valve comprises electrochromic light valve, liquid crystal based light valve (e.g., liquid crystal on silicon, polymer dispersed liquid crystal, dichroic liquid crystal), digital light processing (DLP) valve, or a combination thereof.

The spatial light modulator 36 may be electronically controlled or mechanically adjusted. In one embodiment, adjusting the spatial light modulator 36 may enable changing the mode of the detection system from a high throughput mode to the low throughput mode.

In the illustrated embodiment, the spatial light modulator 36 is disposed between the radiation source 12 and the beam splitter 16. The spatial light modulator 36 may be disposed in the optical path of the reference arm 18, sample arm 20, or both. The spatial light modulator 36 may be configured to modulate incident radiation, resultant radiation, or both in the reference arm 18, sample arm 20, or both. An example location of the spatial light modulator 36 is represented by a reference numeral 50. However, the spatial light modulator 36 may be disposed in various alternate or additional locations in the system 10. The various alternate or additional locations are represented by reference numerals 52, 54, 56, 58 and 60. In embodiments where two or more spatial light modulators are used, the spatial light modulators may be disposed in the one or more locations 50, 52, 54, 56, 58 and 60.

In certain embodiments, a single spatial light modulator may be used in the system 10. In one embodiment, the spatial light modulator 36 may be disposed in a common path for the reference and sample arms 18 and 20, respectively. As illustrated, in one example, the spatial light modulator 36 may be disposed between the radiation source 12 and the beam splitter 16. In another example, the spatial light modulator 36 may be disposed in the path of co-propagating radiation 48, comprising the resultant reference and resultant sample radiation 44 and 42, respectively. In this example, the spatial light modulator 36 may be disposed in the location 60.

In certain embodiments, two or more spatial light modulators may be disposed in the optical engine 15. In one embodiment where two spatial light modulators are used in the system 10, a first spatial light modulator 36 may be disposed in the optical path of the incident radiation for the reference arm 18, location 54, and a second spatial light modulator may be disposed in the optical path of the incident radiation for the sample arm 20, location 52. In another embodiment where two spatial light modulators are used in the system 10, a first spatial light modulator may be disposed in the optical path of the resultant radiation for the reference arm 18, location 58, and a second spatial light modulator may be disposed in the optical path of the resultant radiation for the sample arm 20, location 56. In one embodiment, a first spatial light modulator may be disposed in the optical path of the incident reference radiation light, location 54, and a second spatial light modulator may be disposed in the optical path of the resultant sample radiation, location 56, or vice versa.

The samples may be detected by analyzing interference spectra formed by interference of the co-propagating radiation 48. The interference spectra from the optical engine 15 are received by an image acquisition unit 22. The image acquisition unit 22 acquires image data that includes interference in a spectral domain. The image acquisition unit 22 may comprise an imaging spectrometer. The imaging spectrometer may comprise a combination of a detector and dispersing element. In one embodiment, the dispersing element may comprise a grating. In one embodiment, the grating may be tilted at a determined angle to obtain additional spatial separation of frequencies.

The image acquisition unit 22 may include additional optical elements such as lenses for collimating or focusing the radiation. The acquired image may be processed using a signal processing unit 62. A user interface 64, such as, but not limited to, a graphical user interface (GUI), may be used to allow the user to interact with the detection system 10.

The signal processing unit 62 may comprise a microprocessor, microcontroller or a digital signal processor (DSP). The system 10 may also comprise a storage device (not shown) for at least temporarily storing one or more images. The storage device may comprise, but is not limited to, any suitable hard drive memory associated with the processor such as the ROM (read only memory), RAM (random access memory) or DRAM (dynamic random access memory) of a CPU (central processing unit), or any suitable disk drive memory device such as a DVD or CD, or a zip drive or memory card. The storage device may be remotely located from the signal processing unit 62 or the imaging device, and yet still be accessed through any suitable connection device or communications network including but not limited to local area networks, cable networks, satellite networks, and the internet, regardless whether hard wired or wireless.

Figure 2:
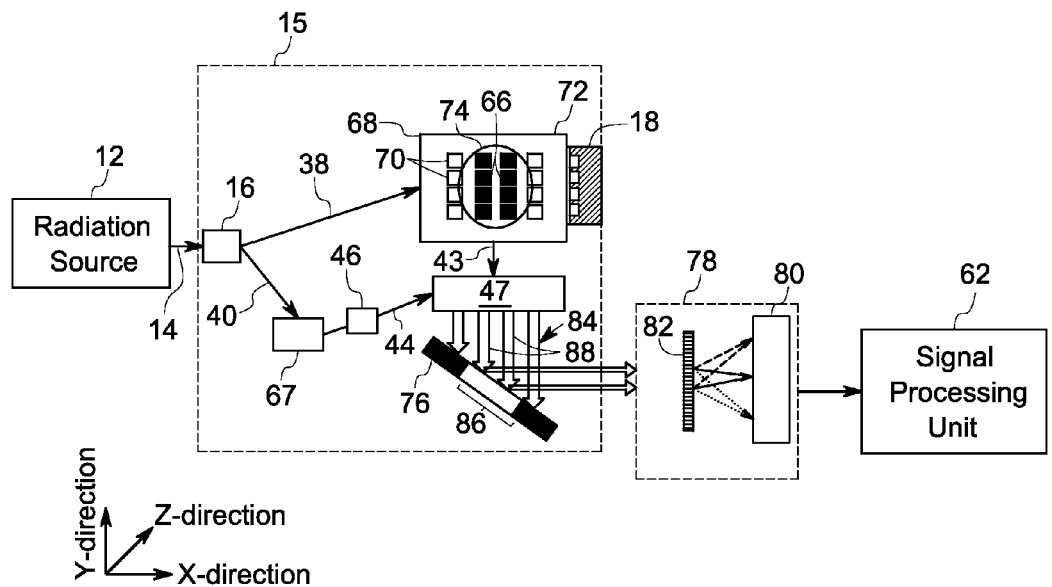
FIG. 2 is a schematic drawing of an example optical engine of FIG. 1, where the optical engine comprises a spatial light modulator operatively coupled to a sensing substrate.

FIG. 2 illustrates an example multimode detection system comprising the optical engine 15. The optical engine 15 comprises an optical arrangement for directing the electromagnetic radiation 14 to the beam splitter 16. The beam splitter 16 divides the radiation 14 into the first portion 38 and second portion 40. The first portion 38 may irradiate one or more samples 66 disposed on the sensing substrate 68, and the second portion 40 may irradiate the reference 67. The samples 66 may be chemical or biological samples. In one embodiment, the samples 66 may be chemically or biologically active samples. The chemically or biologically active samples 66 may produce a determined response when contacted with a chemical or a biological entity, respectively. In one example, the samples 66 may have a time constant optical property. The samples 66 may comprise optically active materials. In one example, the samples 66 may be able to absorb, transmit, or reflect the incident radiation.

In certain embodiments, the reference 67 may comprise conventionally used reference solutions such as, but not limited to, high index solutions or low index solutions wherein the high and low refractive index are the refractive index values that fall outside a resonance range of a device disposed in the optical engine 15, such as a waveguide. In certain other embodiments, the reference 67 may comprise a material with determined or known spectral absorption values. The known spectral absorption values may comprise a known constant value or a known time varying value. In one embodiment, the reference 67 may be a non-absorptive sample. That is, the reference 67 may comprise a material that reflects a major portion of the incident radiation. In certain other embodiments, the reference 67 may be an optical element, such as, but not limited to, a mirror, or a total internal reflection surface.

The sensing substrate 68 may comprise a plurality of sample fields 70 disposed on a side. The sample fields 70 may be spatially separated. In one embodiment, the sensing substrate 68 may comprise an array of sample fields 70. The array of the sample fields may be of varying sizes such as, but not limited to, a 4×4 array, a 6×6 array, or an 8×8 array. Some or all the sample fields 70 may comprise samples.

The sensing substrate 68 may be a spectrally modifying surface that may reflect, absorb, or transmit at least a portion of the incident sample radiation 38. The sensing substrate 68 may comprise a spectrally modifying material for reflected radiation. The sensing substrate 68 may comprise materials, such as, but not limited to, glass, polymer material, silicon (e.g. silicon wafer), or a combination thereof. In one example, the material of the sensing substrate 68 may be configured to transmit a determined wavelength range. The sensing substrate 68 may reflect wavelengths that are outside the detectable wavelength range of an imaging spectrometer 78. In one example, the reflected wavelengths may be detected using an image acquisition subsystem, such as an imaging spectrometer 78.

The sensing substrate 68 may be selected based on the detection techniques that are used. Non-limiting examples of the detection techniques may include surface plasmon resonance (SPR) such as, but not limited to, a localized SPR (LSPR), nano-grating SPR, label-free SPR, or other techniques such as, but not limited to, reflectometric interference spectroscopy (RIfS). In the case of LSPR, the sensing substrate 68 may include a glass substrate having metal structures. In the case of RifS the sensing substrate 68 may include a glass surface. In the case of nano-grating SPR, the sensing substrate 68, may include a glass surface having nano gratings.

The sample fields 70 may be formed on the sensing substrate 68 by processing corresponding portions of the sensing substrate 68. The processing may comprise fabrication techniques such as, but not limited to, etching, patterning, or functionalizing at least portions of the sensing substrate 68 corresponding to the sample fields 70. In one embodiment, portions of a first index layer of the sensing substrate may be etched to form trenches for forming the sample fields 70.

In certain embodiments, at least a portion of the sensing substrate 68 may be identified as a region of interest 74. A corresponding portion in the reference may be identified as a region of interest. The region of interest 74 may comprise one or more sample fields 70. The region of interest 74 may be the region disposed on the sensing substrate 68, where the region comprises sample fields 70 having the samples 66 whose spectral characteristics are to be determined. The sample fields 70 disposed in the region of interest 74 may comprise the same or different samples. The samples 66 disposed in the region of interest 74 may be detected while the samples disposed outside the region of interest 74 may not be detected, thereby resulting in selective detection of the samples 66.

The region of interest 74 may comprise a 1D or 2D array of samples. In one embodiment, subsequent to identifying the region of interest 74 on the sensing substrate 68, the samples 66 may be provided in the sample fields 70 that are disposed in the region of interest 74. The fluidic device 18 may be configured to provide the samples 66 in the sample fields 70 that are disposed in the region of interest 74. In another embodiment, the samples 66 may be disposed in the sample fields 70 prior to identification of the region of interest 74. In this embodiment, the samples 66 may be disposed in the form of an array. Some or all the disposed samples 66 may be detected. The sample array may comprise e a 1D or a 2D array of samples 66.

In one embodiment, at a given time, the sensing substrate 68 may comprise more than one region of interest 74. In this embodiment, the regions of interest may be disposed in two discrete locations on the sensing substrate 68. In another embodiment, a position of the region of interest may vary with respect to time and/or analysis. In this embodiment, a first region of interest may be identified on the sensing substrate 68, and samples disposed in the first region of interest may be detected. Next, a second region of interest may be identified on the sensing substrate 68, and samples disposed in the second region of interest may be detected.

In one embodiment, two or more sample fields 70 in the region of interest 74 may comprise the same sample. The sample may be assigned more than one reflectance peak during imaging reconstruction process. In this embodiment, the size of the array in the region of interest may remain the same; however, during the image reconstruction, data peaks for the same type of sample may appear more than once. The data from the various reflectance peaks representative of the same sample may be used to calculate the surface plasmon resonance (SPR) information for the single sample type. In one example, the data from the peaks may be averaged. Processing the data for one sample from one or more peaks increases the resolution of detection.

In certain embodiments, at least a portion of the sample fields 70 may be functionalized with one or more functionalizing agents. The functionalizing agents may comprise a coating of specific antibodies, proteins, DNA sequences, ligand molecules or amino acid sequences that are sensitive and specific to chemical or biological agents of interest. The functionalizing agents may be present in the form of a layer or a coating, also referred to as a functionalized coating. By changing the functionalizing agents the systems and methods may be used for linear detection or threshold detection of predetermined agents. In one embodiment, the detection may be based on the competitive binding of the sample to the binding sites of the ligand. Same or different ligands may be disposed in the different sample fields 70 of the samples 66.

The functionalizing agents may be disposed in the sample fields 70. Thus, the functionalizing agents may be present in the form of an array of discrete sample-binding regions. The different sample fields 70 may comprise same or different functionalizing agents. For example, one or more of the sample fields 70 may comprise a ligand molecule different than the other sample fields. In one embodiment, all the different sample fields 70 may comprise different ligand molecules. The ligands may comprise one or more of a biopolymer, an antigen, antibody, nucleic acids and hormone ligands. In one example, for antibody binding measurements, an antigen may be immobilized on the sample fields 70 and the sensing substrate may be exposed to a solution containing the antibody of interest, after which binding proceeds.

The functionalizing material may saturate due to high concentrations of the samples in the array, or due to exposure of the sensing substrate 68 to the sample solution for a long period time. In cases where the functionalizing material gets saturated, the corresponding sample field 70 or the sensing substrate 68 may be regenerated to continue the detection. In one embodiment, the sensing substrate 68 may be regenerated to allow the detection system to be used over and over again, thereby reducing the working material required, with a consequent significant cost reduction. In one example, the regeneration of the sensing substrate 68 may be achieved by applying a different solution than previously used. In one example, the sensing substrate 68 may be exposed to a base solution, such as sodium hydroxide, or to an acidic solution, such as, glycine hydrogen chloride buffer having a pH 2.0, to regenerate the sensing substrate. The regeneration of the ligands considerably reduces the cost of the system. In one embodiment, regeneration of the ligands enables detection of different sample solutions. In this embodiment, the ligands are regenerated after detecting existing sample solution in a sample field and before providing the next sample solution in the sample field. In embodiments where the different sample fields 70 may comprise different ligand molecules, the different sample fields 70 may be aligned with a corresponding fluidic channel of a fluidic device having a corresponding ligand molecule.

A definer component 72 may be provided to define the geometry and the number of sample fields 70 on the sensing substrate 68. Also, the contrast between the sample fields 70 and their intermediate regions may be determined by the definer component 72. In certain embodiments, the definer component 72 may be disposed in selected regions of the sensing substrate 68. For example, the definer component may be disposed in regions around the sample fields 70.

In one example, the definer component 72 may be configured to block the light (e.g., by absorbing the light) reflected from the sample fields 70 disposed around the region of interest 74. The blocking of the undesired light reduces the load at the spectrometer 78, and enhances the performance of the device by reducing the noise.

At least a portion of the incident sample beam 30 may interact with the samples 66 disposed in the region of interest 74. At least a portion of the interacted radiation is reflected back as resultant sample radiation 43. The resultant sample radiation 43 may be a reflective radiation or a transmissive radiation. Resultant reference radiation from the reference 67 is generally referred to by reference numeral 45.

In certain embodiments, a path length difference may be introduced in one or more of the sample beam 38, reference beam 40, resultant sample radiation 43, or resultant reference radiation 45 using a phase difference generator 46. The phase difference generator 46 may be disposed in the sample arm or reference arm. The resultant sample radiation 45 from the various samples 66 may combine at a beam splitter 47 with the resultant sample and reference radiation 43 and 45, respectively, to form co-propagating reference and sample beams 84.

In certain embodiments, a spatial light modulator 76 may be operatively coupled to the sensing substrate 68. The spatial light modulator 76 may be configured to modulate the amount of radiation, such as, but not limited to, co-propagating radiation 84, travelling from the sensing substrate 68 towards an imaging spectrometer 78.

The spatial light modulator 76 may be configured to filter out or block the light from the sample fields 70 that are disposed outside the region of interest 74. The sample fields 70 disposed outside the region of interest 74 may or may not comprise samples 66. The region of interest 74 may be selected by the spatial light modulator 76 in the spatial direction, imaging direction, or both. In one embodiment, the spatial light modulator 76 may select the region of interest 74 in the spatial direction. In this example, a variable area component of the spatial light modulator may be disposed in a direction parallel to the spatial direction such that the amount of the co-propagating beams 84 may be controlled along the spatial direction. In one embodiment, the spatial light modulator 76 may be configured to select a region of interest in the spatial direction, and the spectrometer 78 may be configured to select a region of interest along the imaging direction.

Blocking the light from the regions outside the region of interest 74 may facilitate detection of the samples 66 in the region of interest 74 with enhanced resolution. In one example, the light intensity of the incident radiation 14 may be increased such that the reflected light intensity from the samples 66 disposed in the region of interest 74 may be approximated to the total light intensity for near saturation of the imaging spectrometer 78.

In examples where the variable area spatial light modulator is used, the mode of the detection system may be changed by changing the area of the spatial light modulator 76. The area of the spatial light modulator 76 may be adjusted such that an area 86 of the spatial light modulator 76 is configured to allow the portion 88 of the radiation 84 to pass through the spatial light modulator 76. In one embodiment, the spatial light modulator 76 may be configured to be turned off or operatively decoupled for high throughput applications. In this embodiment, the spatial light modulator may or may not be disposed in the optical engine 15 during the high throughput application.

Although in the illustrated embodiment, the region of interest 74 is illustrated as a region disposed in the center of the sensing substrate 68, the region of interest 74 may be disposed in any portion of the sensing substrate 68. Depending on the position of the region of interest 74, the area 86 and position of the spatial light modulator 76 may be determined to facilitate light from the region of interest 74 to travel to the spectrometer 78.

The samples 66 disposed in the region of interest 74 in the spatial direction may be spectrally separated using the phase difference generator 46. The samples 66 disposed along an imaging direction may be spectrally separated using the imaging spectrometer 78. The co-propagating radiation 84 interfere at the imaging spectrometer 78 and produce interference spectra. The path length difference introduced in the sample arm or the reference arm using the phase difference generator 46 may be translated to the phase difference in the interference spectra. Introducing the phase difference in the sample beam 38, reference beam 40, resultant sample radiation 43, or resultant reference radiation 45 provides a condition under which interference between the resultant beams from the reference and samples may occur giving rise to intensity variations in the interference spectra. The phase difference introduced in the incident radiation 38 or 40, or the resultant radiation 43 or 45 may be present in the interference spectra.

The phase difference may be introduced in a first direction, and the imaging may be carried out in a second direction different from the first direction. Imaging in a direction different from that in which the phase difference is introduced, resolves the samples 66 in both first- and second-directions (e.g., x- and y-directions). In one example, the phase difference generator 46 may introduce a phase difference in an x-direction and the imaging may be done in a y-direction. In this example, the phase difference generator 46 facilitates resolving the samples 66 along the x-direction, and the detector resolves and spatially separates the samples 66 disposed along the y-direction.

In addition to the phase shift caused by the phase difference generator 46, the samples 66 disposed in the sample fields 70 may also contribute to the phase shift in the resultant sample radiation. The phase shift produced by the samples 66, may be a fraction of the phase shift produced by the phase difference generator 46. The small phase shift components contributed by the samples 66 may shift the corresponding fringes in the interference pattern. The shift of the fringes corresponds to the properties of the samples 66 at the sample fields 70. The additional shift in the resultant radiation caused by the samples 66 may be useful in determining the chemical or optical properties of the samples 66.

The imaging spectrometer 78 may include a spectrally separated detector 80 and a dispersing element, such as, but not limited to, a grating 82. In one embodiment, the grating 82 may comprise a diffraction grating. The grating 82 is configured to divide the interference spectra being analyzed into its spectral components. The grating 82 projects the spatially divided elements of the radiation 88 onto the detector 80. The interference spectra formed by the co-propagating radiation 84 may be analyzed and imaged using the imaging spectrometer 78. The intensity of the beam received at the detector 80 may depend on the difference in the path length of the beams in the samples 66 and reference 67.

The spectrally separated detector 80 may be a 2D detector. The spectral frequencies in the interference spectra are separated using the detector 80 and the grating 82. The detector 80 detects a change in the optical properties of the reflected light from the samples 66. The detector 80 may detect the analytes concentration or the chemical or biological composition of the samples 66. The imaging spectrometer 78 may be operatively coupled to the signal processing unit 62 that measures interference spectra acquired by the detector 80. The imaging spectrometer 78 may be coupled to detection circuitry that may form part of the signal processing unit 62. In one example, the detection circuitry may convert current signal to voltage signal. Also, the detection circuitry may amplify the signal received from the imaging spectrometer 78. The detection circuitry may include components, such as, but not limited to, a data processor, for receiving measurements of interference pattern from the detector 80, such as a spectrometer, and for conducting analysis thereon, wherein the analysis comprises determining a parameter of an interference spectra. Non-limiting examples of such parameters may include frequency, phase, and intensity of the interference fringes.

The detector 80 may be a photo-detector, a spectrometer, or a charge-coupled device (CCD), complementary metal oxide semiconductor (CMOS), a photodiode (such as an avalanche photodiode), solid state photomultiplier tube (PMT), image receptor, or a camera for measuring reflected light from the sample over a selected range of wavelengths. In embodiments where the detector 80 is a CCD or a camera, the detector 80 may record the spectra of the reflected light from the sample.

For each of the samples 66 on the sensing substrate 68 there may be a corresponding column or row in the spectrometer 78 that measures the interference spectra of the corresponding sample on the sensing substrate 68. If the imaging is performed in a y-direction (which is e.g., a direction of columns), the different samples in a column are individually identified. However, for the samples 66 disposed in x-direction (which is e.g., a direction of rows) the different samples in a row are separately identified by introducing a phase difference using the phase difference generator 46. After imaging using the Fourier transform, the samples 66 in the 2D array of samples are individually identified by the detector.

The radiation source 12 provides a sample beam 38 and a reference beam 40. The sample beam 38 is directed towards the samples 66 on the sensing substrate 68. The reference beam 40 is directed towards the reference 67. The size of the sample beam 38 may be large enough to cover the samples in the region of interest 74, or the array of the sample fields on the sensing substrate 68. In one embodiment, the sample beam 38 may be directed to multi-spot generator optics to produce two or more spatially-spread discrete spots. In one example, the spatially-spread discrete spots are incident on a 2D array of samples. In one example, each of the spatially-spread discrete spots corresponds to a sample from the array of samples 66.

The resultant reference radiation 45 and resultant sample radiation 43 may interact with the spatial light modulator 76 before being received by the spectrometer 78. The spatial light modulator 76 may be configured to select region of interest of the reflected light (reflectance). The region of interest of reflectance corresponds to the region of interest 74 of the sensing substrate 68. In other words, the region of interest of reflectance corresponds to the reflectance of the samples disposed in the region of interest 74.

Although not shown, the optical engine 15 may also include other optical elements such as lenses, filters, and collimators. For example, a lens each may be disposed in the reference arm and the sample arm to direct the radiation to the detector.

The phase difference obtained between the reference 67 and samples 66 may be used to spatially separate the various sample locations with respect to the spectral characteristics of the samples corresponding to those sample locations. The imaging of the locations of the samples 66, for example a 2D array of samples, may be obtained by reconstructing absorption spectra of the samples 66 of the region of interest 74 using signal processing algorithms, such as, but not limited to, Fourier transform. Information regarding locations of the reference samples may be provided to the detector 80. In certain embodiments, the samples 66 may be imaged in a single shot. Signal process algorithms may be used to determine the spatially separated points (samples 66) from the acquired spectra without movement of any mechanical part or the reference beam, thereby improving the imaging speed.

A resultant radiation corresponding to a sample may expand over a certain number of pixels in the detector 80. Each row (samples disposed along the spatial direction) in the region of interest may occupy a row of pixels on the detector 80. In one example, where one or more columns are selected as a region of interest, the same area of the detector 80 may be used even with the reduced number of samples to be detected. Hence, more light may be detected per sample by the pixels of a row. Thereby increasing the resolution of the detection system.

The detection system may be used to determine the adsorption from the gas phase, as well as from liquid solutions, in sample fields comprising the detection elements. In particular, the adsorption of biological molecules such as DNA, proteins, antibodies, and enzymes from aqueous solutions may be monitored in situ with the detection system. Advantageously, the detection system provides wavelength stability and measurement reproducibility, fast data acquisition rates and high signal-to-noise outputs, and broadened spectral ranges.

A computer may be used to process and display the signals and may form part of the signal processing unit 62. The computer may be used to generate a variety of quantitative and qualitative measures. For example, in quantitative measurements, the abscissa may represent time and the ordinate may represent the percentage of concentration of an analyte. In addition, the computer may have a spectra library, which stores the information regarding the spectral characteristics of various elements or chemical compounds. This spectra library may be used to identify unknown samples by comparing the spectral information received from an unknown sample with spectral patterns retained in the library, and identification of the unknown substance may be made by comparison.

The detection and imaging system may be used in different detection techniques to obtain a one-shot/simultaneous detection for 1D or 2D array of samples. The sensing substrate may be modified depending on the different applications. Also, the relative position of the camera and the detector may be changed depending on the application.

Figure 3:
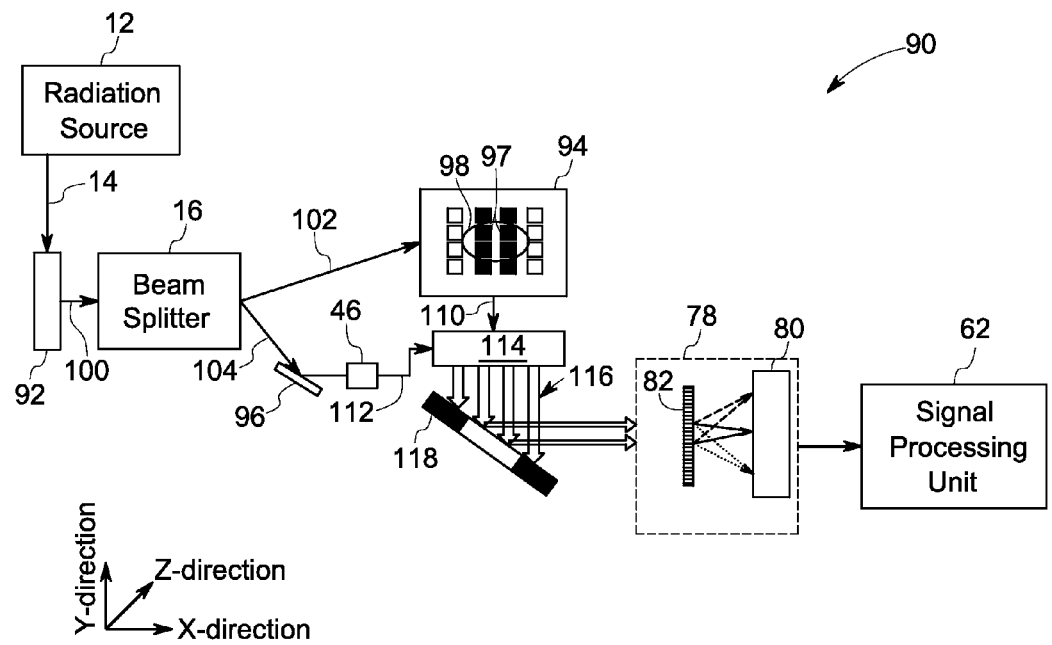
FIG. 3 is a schematic drawing of an example optical engine of FIG. 1, where the optical engine comprises a beam reformer operatively coupled to a radiation source and a spatial light modulator operatively coupled to a sensing substrate.

FIG. 3 illustrates another example embodiment of a detection system, where the detection system 90 comprises a beam reformer 92 operatively coupled to the radiation source 12. The beam reformer 92 may be disposed between the radiation source 12 and the beam splitter 16. In one embodiment, the beam reformer 92 may be used to define regions of interest on the sensing substrate 94 and/or the reference 96. The beam reformer 92 may be configured to pattern the radiation 14 from the source 12 to define a region of interest 98. In one embodiment, the beam reformer 92 may be configured to at least partially block the radiation 14 from the source 12 from reaching the sensing substrate 94 and/or reference 96.

The beam reformer 92 may comprise a physical mask (patterned film of a suitable material) or a digital pattern. The beam reformer 92 may include a light absorbing material. Non-limiting suitable materials for the beam reformer 92 may comprise multilayered structures of one or more light absorbing materials, semiconductors, polymers (e.g., photoresist polymers), or a combination thereof.

In one example, the beam reformer 92 may comprise multi-spot generator optics to produce one or more spatially-spread discrete spots. In one example, the spatially-spread discrete spots are incident on the sample fields 97 disposed in the region of interest 98. In one example, each of the spatially-spread discrete spots corresponds to a sample disposed in the region of interest 98.

The radiation source 12 provides the radiation 14. The radiation 14 is directed towards the beam reformer 92. The reformed/patterned radiation 100 is patterned. The patterned radiation 100 is split in two parts at the beam splitter 16, namely, a sample beam 102 and a reference beam 104. The sample beam 102 is patterned radiation configured to selectively irradiate the sensing substrate 94 to provide resultant sample radiation 110. The sample beam is configured to irradiate samples 97 disposed in the region of interest 98 on the sensing substrate 94. The reference beam 104 is patterned radiation that is configured to selectively irradiate portions of the reference sample 96. The resultant reference radiation is passed through a phase difference generator 46.

The phase differenced reflected reference radiation 112 and resultant sample radiation 110 may combine at a beam splitter 114 to form a co-propagating radiation 116 before interacting with the spatial light modulator 118 before being received by the spectrometer 78. The spatial light modulator 118 may be configured to further select the region of interest in the co-propagating resultant sample and reference radiation 98 and 100, respectively, represented by reference numeral 116. In one example, the spatial light modulator 118 may be configured to filter out radiation from regions adjacent the sample fields 97 which are radiated using the patterned radiation 100 of the sample beam 102.

In one embodiment, the beam reformer 92 may be configured to provided patterned radiation 102 to select the region of interest in the first direction on the sensing substrate 94. The spatial light modulator 118 may be configured to select a region of interest in the second direction. For example, the beam reformer 92 may be configured to irradiate samples disposed in one or more rows, and the spatial light modulator 118 may be configured to allow resultant radiation corresponding to one or more columns to reach the detector 80. As a result, the beam reformer 92 and the spatial light modulator 118 may together define a region of interest on the sensing substrate 94.

Figure 4:
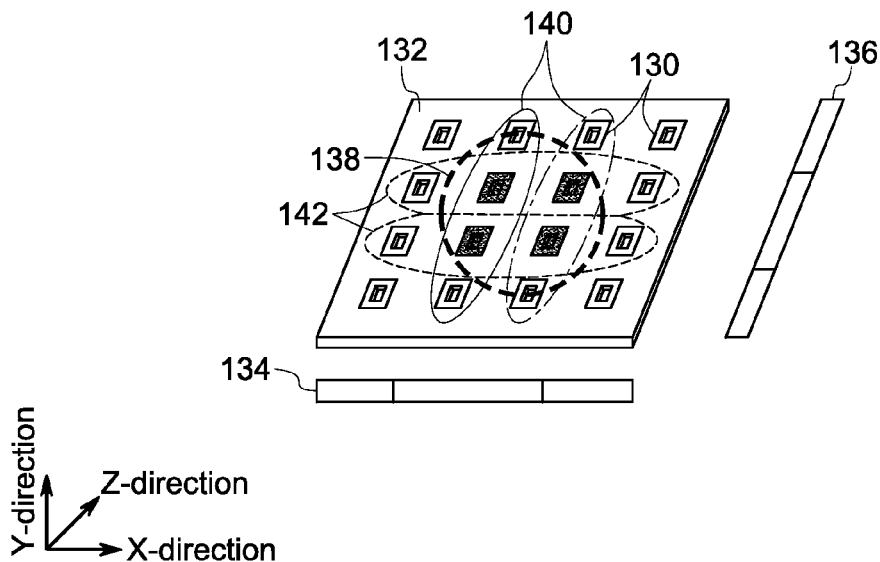
FIG. 4 is a schematic drawing of an example sensing substrate coupled to two spatial light modulators configured to define a region of interest on the sensing substrate.

FIG. 4 illustrates a multimode detection and imaging system comprising a sensing substrate 132 operatively coupled to spatial light modulators 134 and 136. The combination of the two spatial light modulators 134 and 136 may be used to select one or more sample fields 130 disposed on a sensing substrate 132. The spatial light modulators 134 and 136 may together define a region of interest, generally represented by reference numeral 138, on the sensing substrate. In one embodiment, the spatial light modulators 134 and 136 may be simultaneously or consecutively operated. For example, the spatial light modulators 134 and 136 may be simultaneously operated to define the region of interest 138. The spatial light modulator 134 may facilitate selection of a region of interest along the spatial direction. For example, the spatial light modulator 134 may facilitate selection of columns 140. The spatial light modulator 136 may facilitate selection of a region of interest along the imaging direction. For example, the spatial light modulator 136 may facilitate selection of rows 142. In combinations, the spatial light modulators 134 and 136 may define the region of interest 138 comprising common sample fields 144 disposed in the columns 140 and the rows 142.

Figure 5:
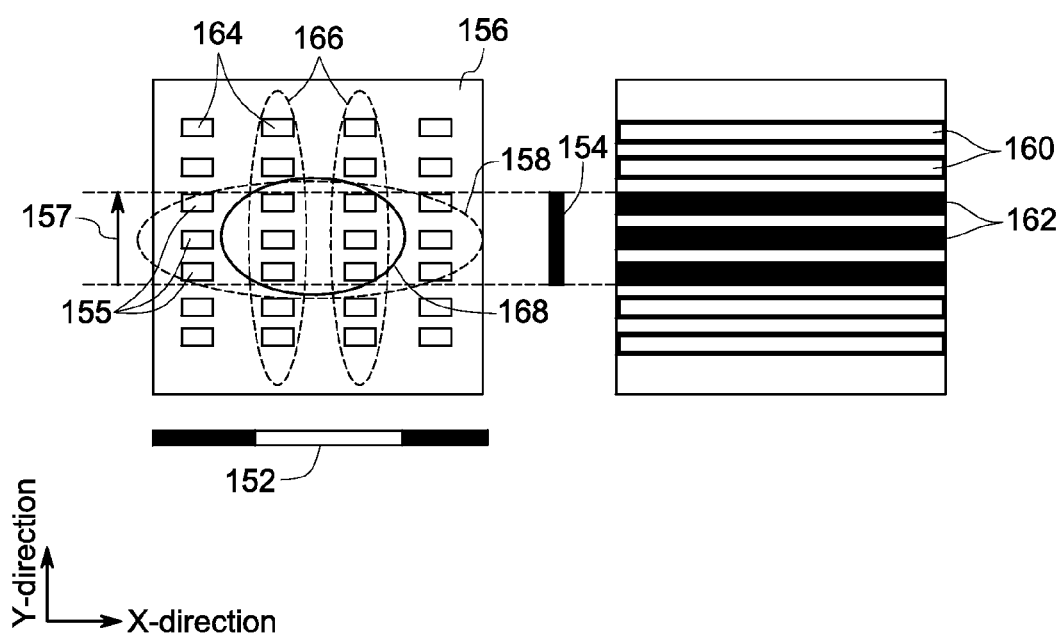
FIG. 5 is a cross-sectional view of an example region of interest disposed along an imaging direction.

FIG. 5 illustrates an embodiment where a spatial light modulator 152 is used in conjunction with a dispersing element, such as a grating 154, to define a region of interest 168 on a sensing substrate 156. The spatial light modulator 152 may be configured to select one or more columns 166 of the samples 164, and the grating 154 may be configured to select a region of interest 158 comprising the rows 155 of the samples 164. Accordingly, the spatial light modulator 152 and the grating 154 in combination may define the region of interest 168. In one embodiment, the grating 154 may be a part of an imaging spectrometer. The grating 154 may be configured to select the region of interest 155 in the imaging direction (arrow 157). In one embodiment, the grating 154 may be configured to filter out radiation corresponding to one or more rows from being received by the imaging spectrometer. In this embodiment, some of the pixels (comprising rows or columns) of a detector of the imaging spectrometer may not be used for detection purposes as the grating 154 may not project data corresponding to the samples disposed outside the region of interest 168. For example, some of the rows 160 of the detector may not be used for imaging, whereas rows 162 may be used to image the samples 164 disposed in the region of interest 168. In one example, detection frame rate of the detector may be increased by selecting the region of interest in the detector in the imaging direction 157.

Figure 6:
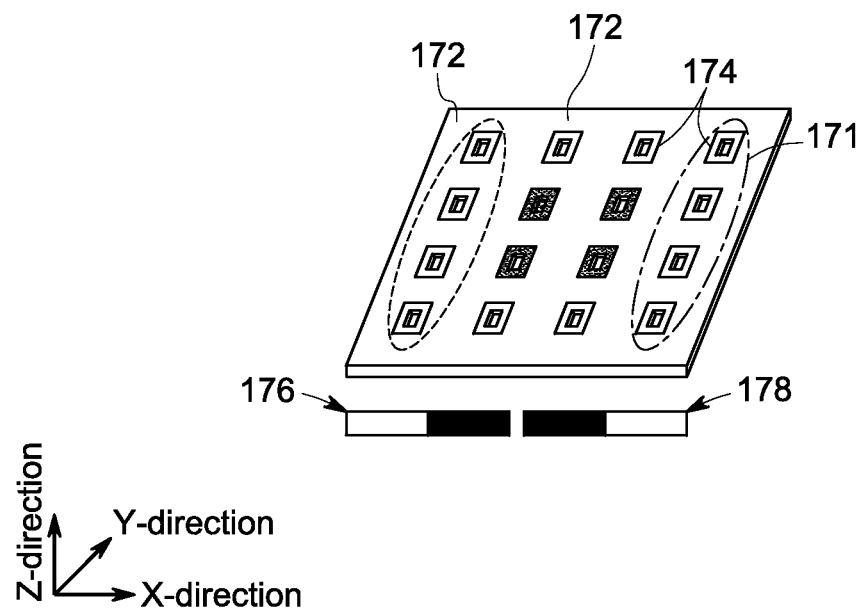
FIG. 6 is a schematic drawing of an example arrangement employing two spatial light modulators to define regions of interest disposed in discrete portions of the sensing substrate.

FIG. 6 illustrates an embodiment where two different regions of interest 170 and 171 are selected on a sensing substrate 172. The regions of interest 170 and 171 may be selected by employing two spatial light modulators 170 and 171.

In the illustrated embodiment, the regions of interest 170 and 171 are disposed in two discrete locations on the sensing substrate 172. In one embodiment, the regions of interest 170 and 171 may be connected. For example, the regions of interest 170 and 171 may comprise common sample fields 174. In one embodiment, the two regions of interest 170 and 171 may be used for different analysis. In one example, the regions of interest 170 and 171 may co-exist in time. In this embodiment, the two spatial light modulator 176 and 178 may be simultaneously in operative association with the sensing substrate 172. For example, the two spatial light modulators 176 and 178 may be turned on at a given time. In one embodiment, a first region of interest (e.g., region of interest 170) may be identified on the sensing substrate 172, and samples disposed in the first region of interest 170 may be detected. Next, a second region of interest (e.g., region of interest 171) may be identified on the sensing substrate 172, and samples disposed in the second region of interest 171 may be detected. In this embodiment, the two spatial light modulators 176 and 178 may be turned on and off sequentially. A fluidic device may be configured to provide samples to the sample fields 174 disposed in the regions of interest 170 and 171 on the sensing substrate 172. The fluidic device may be configured to simultaneously or sequentially provide samples to the sample fields 174 disposed in the regions of interest 170 and 171.

Figure 7:
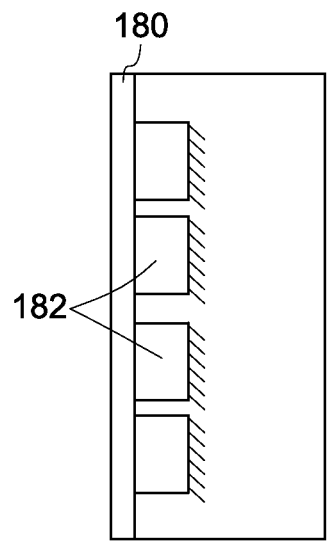
FIG. 7 is a cross-sectional view of an example sensing surface configured for free-solution SPR.

As illustrated in FIG. 7 the sensing surface 180 in the SPR may be configured for free-solution (label free) SPR. The sample fields 182 may be enclosed volumes (e.g., channels, cavities) that comprise one or more functionalizing agents, such as, but not limited to, ligand molecules. One of the sample fields 182 may be configured to receive the sample solution or act as a reference sample.

Figure 8:
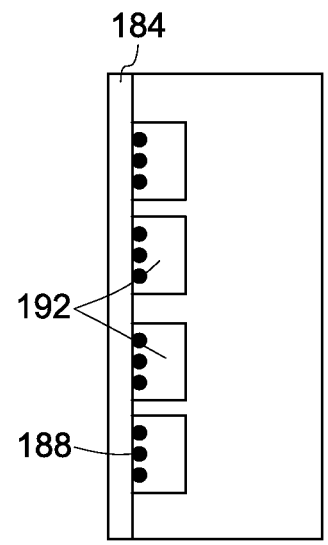
FIG. 8 is a cross-sectional view of an example sensing surface configured for localized SPR.

As illustrated in FIG. 8, the sensing surface 184 in the SPR may be configured for localized SPR (LSPR). The sample fields 186 may comprise electrically conductive structures 188 disposed at least in portions of the sample fields. One of the sample fields 186 may be configured to receive the sample solution, or act as a reference sample. Alternatively, the thin metal film, such as, but not limited to, gold or silver, that is present to enable SPR phenomenon, may be patterned/textured to form the electrically conductive structures. In one embodiment, a patterned film may be used.

Resonance conditions of the LSPR may depend on the refractive index and dielectric constant of the environment surrounding the electrically conductive structures 188. The incident radiation interacts with the localized plasmons on surfaces of the electrically conductive structures 188. A change in the resonance conditions may be detected by measuring a change in the interference spectrum of the resultant projected to and transmitted through the electrically conductive structure of the sample fields. In one example, a biological reaction may cause a change in the dielectric constant of the electrically conductive structures 188 this change may be utilized for detection. In another example, an occurrence of an antigen-antibody reaction around the electrically conductive structure may be detected using the LSPR. In another embodiment, isolated particles may be disposed on the thin metal film. Non-limiting examples, of electrically conductive structures may include silver particles. The particles may be nanoparticles or microparticles.

Figure 9:
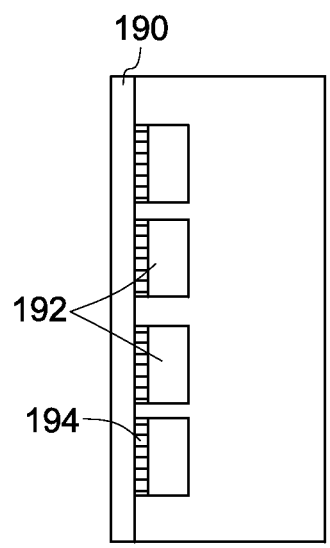
FIG. 9 is a cross-sectional view of an example sensing surface configured for nano-grating SPR.

FIG. 9 illustrates a nano-grating SPR arrangement comprising a transmitting substrate 190 (such as a glass substrate). The arrangement comprises a grating structure 192 disposed on the transmitting substrate 190. The grating structure 192 may be present in the form of a patterned film. Sample solutions may be disposed in sample fields 194 present on the sensing surface formed by the substrate 190 and the grating structure 192 to generate SPR phenomenon. Non-limiting examples of the patterned film may comprise a gold film, silver film, copper film, or combinations thereof. In one example, the grating structure may comprise a gold film disposed on a silver film. The grating structure 192 may include, but is not limited to, gold, silver, copper, or combinations thereof. The grating structure 192 may be a periodic metallic grating structure. In one embodiment, the grating structure 192 may comprise a spacing of between 50 and 500 nm between the gratings. The grating structure 192 may be fabricated using fabricating techniques, such as, but not limited to, nano-imprinting technology, E-beam lithography, ultraviolet lithography, interference lithography, or other nanometric technologies, which are configured to achieve nano-metric structures.

Figure 10:
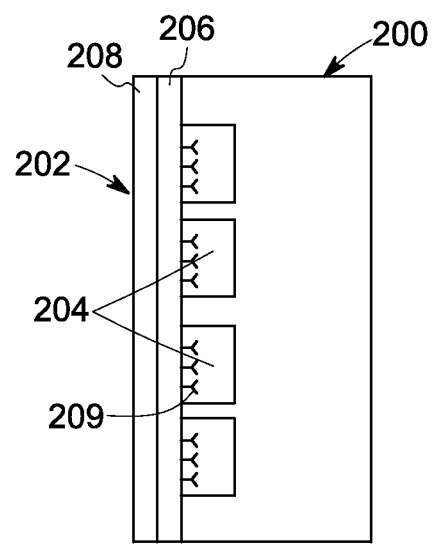
FIG. 10 is a cross-sectional view of an example sensing surface configured for reflectometric interference spectroscopy.

FIG. 10 illustrates an example of a RIfS device 200. The device 200 comprises a sensing surface 202 having sample fields 206. The device 200 comprises a sensing surface 202 having sample fields 204. The sensing surface 202 may comprise a multilayered structure 206 disposed on a transmitting substrate 208. In one example, the multilayered structure 206 comprises a plurality of layers. The various layers of the plurality of layers may comprise silica layers, high refractive index layers (such as, but not limited to, tantalum oxide layer). Beams incident on samples may be at least partially reflected and transmitted at phase boundaries formed between two adjacent layers of the multilayer structure 206. The reflected beams from the various samples may superimpose resulting in an interference spectrum. One or more samples may be configured to act as reference samples. In one embodiment, one or more layers of the multilayer structure 206 may be functionalized using functional agent 209 to facilitate interaction of a portion of the layer with target molecules. Interaction of the functionalized layers with the target molecules may provide a change in a thickness and the refractive index of the functionalized layers. Optical thickness is a product of physical thickness and refractive index, the optical thickness (pathlength) may be changed by changing the physical thickness and the refractive index of the layer. A change in the optical thickness of one or more layers of the plurality of layers may result in a modulation of the interference spectrum. Monitoring the modulation of the interference spectrum over time may be used to observe the binding behavior of the target molecules.

The arrangements illustrated in FIGS. 7-10 may be used in the optical engine 15 of FIGS. 1 and 3, and sensing substrates of FIGS. 4-6, to provide multimode detection and imaging system.

Figure 11:
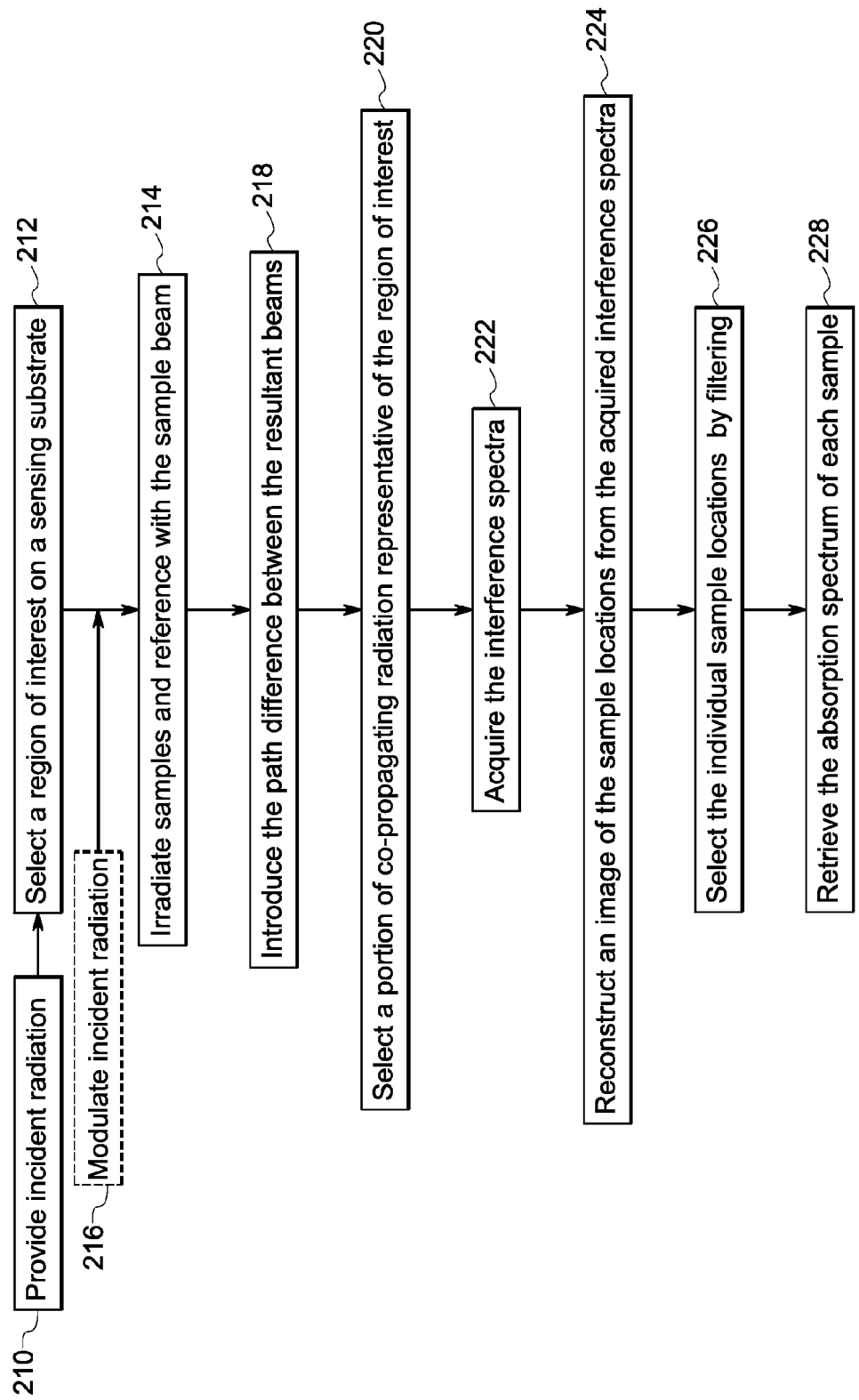
FIG. 11 is a flow chart of an example method for reconstructing an image of spectral characteristics for one or more sample locations for multimode detection and imaging of one or more samples.

FIG. 11 illustrates an example of a method for selectively detecting one or more samples. At step 210, an incident radiation is provided. The incident radiation may be provided by a single source, such as a broadband light source, or multiple sources, such as a plurality of light emitting diodes. In one embodiment, the incident radiation may be patterned.

At step 212, a region of interest is determined on the sensing substrate. The region of interest may comprise samples whose spectral characteristics are to be imaged. In one example, sample fields may be identified, and samples whose spectral characteristics are to be imaged may be disposed in these sample fields, the region having the sample fields may be referred to as the region of interest.

At step 214, the samples and reference may be irradiated with the incident radiation. The incident radiation may be split such that one portion of the incident radiation may be used to illuminate the reference, and the other portion may be used to illuminate the samples disposed on the sensing substrate. In one example, the other portion may be used to illuminate only the samples disposed in the region of interest. The incident radiation may be used to irradiate samples and reference. The incident radiation may be used to irradiate some or all portions of the samples and reference.

Optionally, at step 216, the incident radiation may be modulated prior to irradiating the sample and reference to at least partially define a region of interest. In this example, a portion of the incident radiation may be blocked from reaching the sensing surface. The remaining portion of the incident radiation may be used to define the region of interest. The incident radiation may be patterned prior to splitting. For example, the incident radiation may be used to irradiate sample fields disposed in the region of interest. Alternatively, the incident radiation may be used to irradiate the entire array of sample fields disposed on the sensing substrate. The incident radiation may be patterned such that selective portions of the sensing substrate and reference sample are irradiated.

In examples where the mode of detection comprises a low throughput and high resolution detection, that is, the examples where only some of the sample fields are selected for disposing the samples to be detected, the light intensity of the incident radiation may be increased such that the reflected light from the samples in the region of interest is about the same as near saturation light intensity of the spectrometer.

The resultant sample and reference beams may be reflective or transmissive beams. At step 218, a path length difference may be introduced in a determined direction in the samples disposed in the region of interest. The path length difference may be introduced in the incident radiation or the resultant radiation. The path length difference may be introduced in the spatial direction. In one example, the spatial direction may be perpendicular to a ruling direction of the grating of the spectrometer. Assuming that the direction of traversing the samples in a row is x-direction, which is also a direction perpendicular to the ruling direction of the grating. The phase difference may be introduced in the x-direction. In this way, the samples disposed in a particular row may have a path length added in their corresponding incident beams or resultant reflected beams.

The phase separated reference and sample radiation may be allowed to co-propagate. At step 105, at least a portion of the co-propagating radiation may be spatially modulated to represent a region of interest. In one example, spatially modulating may comprise filtering or blocking at least a portion of the co-propagating radiation and allowing the remaining portion representative of the region of interest to irradiate the region of interest. A spatial light modulator may be used to block the resultant radiation from reaching the sample fields disposed outside the region of interest. In one example, a region of interest may be identified on the sensing substrate. In another example, a region of interest may be selected in the resultant radiation. In examples where the region of interest is not defined prior to irradiating the samples, the region of interest may be defined at this step (220). In these examples, of reflectance may be selected from the resultant sample beam. The region of interest may be selected by modulating the resultant sample beam before the resultant sample beam is received by the spectrometer.

In one example, the region of interest may be defined by adjusting the variable area of one or more spatial light modulators disposed in the spatial direction, imaging direction, or both. Alternatively, or in addition, the orientation of the grating may be adjusted to select the region of interest.

The spatial light modulator may be configured to be turned on and off or operatively coupled and decoupled while switching from one mode of operation to another. For example, the spatial light modulator may be turned off or decoupled for high throughput applications. In this example, the spatial light modulator may or may not be disposed in the optical engine.

In one example, the sample fields may be regenerated to facilitate use of the sensing substrate from one mode to another. For example, the sensing substrate may be exposed to a base solution, such as sodium hydroxide, or to an acidic solution, such as, glycine hydrogen chloride buffer having pH 2.0, to regenerate the sensing substrate.

In some examples, a detectable wavelength range from the co-propagating light may be selected using a dispersing element. In one example, the detectable wavelength range may be selected by adjusting an orientation of the grating. In one example, a ruling of the grating may be changed to zoom in or zoom out of a given wavelength range. For example, the ruling of the grating may be increased for zooming in to a wavelength range.

In one example, an orientation of the grating may be adjusted depending on the wavelength range of detection. For example, a center position of the wavelength range of detection of the spectrometer may be tuned by rotating the grating. The wavelength range of detection may refer to a wavelength range that may be imaged on the detector of the spectrometer. The wavelength range of detection may depend on various factors and parameters of the system, such as, but not limited to, an incidence angle of radiation on the sensing substrate, refractive index of the optics (prism), ruling of the grating, physical dimensions of the detector, dynamic wavelength range, or a combination thereof.

The dynamic refractive index range of a system refers to a range of bulk refractive indices within which the detection may be realized in the system. In the case of SPR detection, a dynamic range of the system refers to a range of refractive indices within which the SPR phenomenon may be realized in the system. The dynamic range of the system may depend on the wavelength range of detection. In one example, dynamic range of the system may be in a range from about 1.32 to about 1.41. A dynamic wavelength range of a system refers to a wavelength range for which spectra for bulk refractive indices may be detected by the detector.

In certain examples, the system may be configured to zoom in to a desirable wavelength range of detection and thus dynamic range by modifying a ruling of the grating. Zooming into the wavelength range may facilitate increased detection resolution. In one example, for a given wavelength range of detection of 650 nm to 850 nm, a grating having 600 grooves may be configured to provide a dynamic range of about 1.33 to about 1.48. By changing the ruling of the grating from 600 to 1200, the wavelength range may be zoomed into from about 700 nm to about 800 nm, and refractive index may be zoomed into from about 1.33 to 1.35, thereby increasing the resolution of detection At step 220, a portion of the co-propagating radiation that is representative of the region of interest may interfere to form interference spectra.

At step 222, the interference spectra may be acquired. The interference spectra may be acquired by the imaging spectrometer. The interference spectra may be received by the detector. Spectral differences may be produced in the interference spectra by passing the interference spectra through a grating before receiving the spectra by the detector. The spectral difference may be produced by passing the interference spectra through a grating before receiving the spectra by a 2D detector. The samples of a particular column may be spectrally resolved using a 2D detector.

At step 224, sample locations of the samples disposed in the region of interest may be reconstructed from the interference spectra by using signal processing algorithms. In one example, a Hilbert transform may be applied to the data representing the interference spectra followed by an Inverse Fourier Transform to reconstruct the sample point locations. The various sample locations are separately identifiable in the reconstructed image using the induced path length difference.

At step 226, filtering may be performed on the reconstructed image to separate the individual sample locations. The individual sample locations may be filtered depending on frequencies used by the individual samples. In one example, a windowing technique may be used to separate the individual sample points. In another example, the data may be analyzed using time frequency analysis to determine spectra and/or content of the different sample points.

At step 228, the absorption spectra of each sample may be retrieved. In one example, a Fourier Transform may be applied to retrieve the frequencies corresponding to the different spatial locations of the samples.

The systems and methods provide a flexible work flow arrangement for detection and imaging of the one or more samples. The flexible work flow arrangement facilitates time efficient and cost effective systems and methods for selectively detecting samples. Advantageously, the selective detection of the samples requires minimal or no changes in the set-up of the device. For example, the same fluidic device, sensing substrate, spectrometer, may be employed for detecting varying number of samples. In certain embodiments, samples may be disposed in all of the sample fields, and some or all the disposed samples may be detected. In certain other embodiments, only some (one or more) of the sample fields may comprise samples that are to be detected. The number of samples to be detected may be varied depending on the requirement. The detection may be performed at a desirable resolution value by varying the throughput of the system.

The systems and methods facilitate selecting one or more samples from an array of samples. The systems and methods enable detection of a varying number of samples with the same set-up, thereby making the system cost effective and the method time efficient. The resolution of the detection may be a greater number of samples may be detected at a moderate resolution. In another embodiment, a fewer With a plurality of samples, the systems and methods do not require repeating the method steps for each sample of the plurality of samples and are configured to simultaneously detect (and image) a plurality of samples disposed in the sample array. The methods do not require mechanical movement of parts of the systems for simultaneous detection of the plurality of samples. The absence of mechanical movement facilitates a longer lifetime of the instruments and provides relative immunity to the system from mechanical vibrations, which may be caused from moving instrument or instrument parts.

While only certain features of the invention have been illustrated and described herein, many modifications and changes will occur to those skilled in the art. It is, therefore, to be understood that the appended claims are intended to cover all such modifications and changes as fall within the scope of the invention.

The invention claimed is:

1. A multimode detection system for detecting one or more samples, comprising:
   an electromagnetic radiation source;
   a reference arm;
   a sample arm comprising a sensing substrate having a plurality of sample fields, wherein the sample fields are configured to receive the one or more samples;
   a phase difference generator configured to introduce one or more pathlength differences in the reference arm, the sample arm, or both;
   a spatial light modulator disposed in an optical path of the reference arm, the sample arm, or both, wherein the spatial light modulator is configured to spatially modulate incident radiation, resultant radiation, co-propagating radiation, or combinations thereof, wherein the spatial light modulator is configured to select a region of interest in a spatial direction, and wherein the spatial light modulator comprises a variable area light valve; and
   an imaging spectrometer configured to discriminate between two or more spatially separated sample fields, wherein the imaging spectrometer includes a detector and a grating, wherein the grating comprises a ruling, wherein the ruling is changed to zoom to a given wavelength range generating multiple optical modes,
   and wherein an area of the variable area light valve that allows light from the sensing substrate to reach the imaging spectrometer is adjusted to modulate an amount of co-propagating radiation that reaches the imaging spectrometer.

2. The multimode detection system of claim 1, wherein the spatial light modulator comprises a mechanical light valve, a micro-mechanical light valve, a micro-opto-electromechanical structure, a non-mechanical light valve, or combinations thereof.

3. The multimode detection system of claim 2, wherein the mechanical light valve comprises a micro-electro mechanical system based valve, a variable slit device, or a combination thereof.

4. The multimode detection system of claim 2, wherein the non-mechanical light valve comprises a liquid crystal based light valve, a digital light processing valve, an electrochromic light valve, or combinations thereof.

5. The multimode detection system of claim 1, further comprising a definer component disposed on at least a portion of the sensing substrate.

6. The multimode detection system of claim 1, further comprising a fluidic device operatively coupled to the sensing substrate, wherein the fluidic device is configured to selectively dispose samples in one or more sample fields.

7. The multimode detection system of claim 1, wherein the spatial light modulator is operatively coupled to the electromagnetic radiation source.

8. The multimode detection system of claim 1, wherein at least one sample field comprises a functionalizing agent.

9. The multimode detection system of claim 1, wherein the phase difference generator comprises a dielectric material, a stack of glass plates, a liquid crystal, a computer generated hologram, or combinations thereof.

10. The multimode detection system of claim 1, comprising two or more spatial light modulators, wherein the two or more spatial light modulators are operatively coupled to the sensing substrate, and a reference to modulate co-propagating resultant radiation.

11. The multimode detection system of claim 10, wherein a first spatial light modulator is configured to define a region of interest in the spatial direction, and wherein a second spatial light modulator is configured to define a region of interest in an imaging direction.

12. The multimode detection system of claim 1, wherein the imaging spectrometer comprises a two-dimensional detector operatively coupled to the grating.

13. The multimode detection system of claim 12, wherein the grating is configured to select a range of wavelengths of interest in a dynamic wavelength range.

14. A multimode detection system for detecting one or more samples, comprising:
   an electromagnetic radiation source;
   a reference arm;
   a sample arm comprising a sensing substrate having a plurality of sample fields configured to receive the one or more samples;
   a fluidic device operatively coupled to the sensing substrate, wherein the fluidic device is configured to selectively dispose samples in one or more sample fields;
   a phase difference generator configured to introduce one or more pathlength differences in the reference arm, the sample arm, or both;
   a spatial light modulator disposed in an optical path of the reference arm, the sample arm, or both, wherein the spatial light modulator is configured to spatially modulate incident radiation, resultant radiation, co-propagating radiation, or combinations thereof, wherein the spatial light modulator is configured to select a region of interest in a spatial direction, and wherein the spatial light modulator comprises a variable area light valve, and wherein an area of the variable area light valve that allows light from the sensing substrate to reach a imaging spectrometer is adjusted to modulate an amount of co-propagating radiation that reaches the imaging spectrometer;
   a grating configured to receive the modulated light from the spatial light modulator, wherein the grating comprises a ruling, wherein the ruling is changed to zoom to a given wavelength range generating multiple optical modes; and
   a detector operatively coupled to the grating for detecting the modulated light, wherein the grating is configured to direct the modulated light to the detector.

15. The multimode detection system of claim 14, wherein the detector is configured to select a region of interest in an imaging direction.

16. The multimode detection system of claim 1, wherein the electromagnetic radiation source, the reference arm, the sample arm, the phase difference generator, and the spatial light modulator are in a fixed position.

* * * * *